(12) United States Patent
Brown et al.

(10) Patent No.: US 7,993,864 B2
(45) Date of Patent: Aug. 9, 2011

(54) ASSAY FOR IDENTIFYING ANTIBODY PRODUCING CELLS

(75) Inventors: Derek Thomas Brown, Beenham (GB); Lisa Butler, Slough (GB); Karen Dorothy Cromie, Holyport (GB); Meryn Ruth Griffiths, Slough (GB); Alastair David Griffiths Lawson, Hampshire (GB); Daniel John Lightwood, Slough (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 10/537,309

(22) PCT Filed: Dec. 1, 2003

(86) PCT No.: PCT/GB03/05254
§ 371 (c)(1),
(2), (4) Date: Dec. 16, 2005

(87) PCT Pub. No.: WO2004/051268
PCT Pub. Date: Jun. 17, 2004

(65) Prior Publication Data
US 2006/0148012 A1 Jul. 6, 2006

(30) Foreign Application Priority Data

Dec. 3, 2002 (GB) .................................. 0228188.9
Aug. 20, 2003 (GB) .................................. 0319587.2

(51) Int. Cl.
C12P 21/08 (2006.01)
G01N 33/53 (2006.01)

(52) U.S. Cl. ................... 435/7.24; 435/69.6; 435/70.21; 435/71.1

(58) Field of Classification Search .................. None
See application file for complete search history.

(56) References Cited

U.S. PATENT DOCUMENTS

| | | | |
|---|---|---|---|
| 3,865,689 A * | 2/1975 | Goldenberg | 435/70.3 |
| 4,816,397 A | 3/1989 | Boss et al. | 435/68 |
| 5,264,341 A * | 11/1993 | Maciak et al. | 435/7.21 |
| 5,326,696 A | 7/1994 | Chang | |
| 2007/0243564 A1 | 10/2007 | Lawson et al. | |

FOREIGN PATENT DOCUMENTS

| | | |
|---|---|---|
| EP | 0 286 405 A3 | 10/1988 |
| WO | WO 92/02551 A1 | 2/1992 |
| WO | WO 94/09117 | 4/1994 |
| WO | WO 99/58977 | 11/1999 |
| WO | WO 02/44216 A1 | 6/2002 |
| WO | 2005/121789 | 12/2005 |
| WO | 1999/57311 | 4/2010 |

OTHER PUBLICATIONS

Kipps et al, in Weir et al (Eds.), Handbook of Experimental Immunology, vol. 4, Blackwell Scientific Publications, 1986, pp. 108.1-108.9.*
Sternberger, Immunocytochemistry, Prentice-Hall, Inc., 1974, pp. 18-32.*
Stephens et al., "Automation for High-Throughput Identification and Picking of GFP Expressing Colonies", J. Assoc. Laboratory Automation 7(3):41-43 (Jun. 2002).
International Search Report for PCT/GB03/05254 dated Mar. 4, 2004.
International Search Report for PCT/GB2005/002305 dated Nov. 3, 2005.
"Merriam-Webster" online definition for "anti-idiotypic antibody" (pp. 1-2 (Jan. 8, 2009)).
"biology online" definition for "anti-idiotypic antibody" (p. 1 (Jan. 8, 2009)).
"online medical" definition for "anti-idiotypic antibody" (p. 1 (Jan. 8, 2009)).
Babcook, J.S., et al., "A novel strategy for generating monoclonal antibodies from single, isolated lymphocytes producing antibodies of defined specificities," Proc. Natl. Acad. Sci. USA, 1996, 93, 7843-7848.
Bae, S.W.., et al., "Influence of fluorescent antibody probe specificity on flow cytometric analysis of antibody-producing cells," J. of Immunol. Methods, 1996, 189(1), 83-88.
Bird, R.E., et al., "Single-chain antigen-binding proteins," Science, 1988, 242, 423-426.
Holmes, P., et al., "Improved cell line development by a high throughput affinity capture surface display technique to select for high secretors," J. of Immunol. Methods, 1999, 230, 141-147.
Jerne, N.K., et al., "Plaque formation in agar by single antibody-producing cells," Science, 1963, 140, p. 405.
Moav, N., et al., "Biologic activities of lymph node cells fractionated on bovine plasma albumin," J. of Immunol., 1970, 105(6), 1512-152.
Morrison, S.L., et al., "Chimeric human antibody molecules: mouse antigen-binding domains with human constant region domains," Proc. Natl. Acad. Sci. USA, 1984, 81, 6851-6855.
Orlandi, R., et al., "Cloning immunoglobulin variable domains for expression by the polymerase chain reaction," Proc. Natl. Acad. Sci. USA, 1989, 86, 3833-3837.
Reading, C.L., "In vitro immunization for the production of antigen-specific lymphocyte hybridomas," Methods in Enzymology, Langone, J.J., et al. (Eds.), Academic Press Inc., N.Y., 1986, 121, 18-27.
Riechmann, L., et al., "Reshaping human antibodies for therapy," Nature, 1988, 322, 323-327.

(Continued)

Primary Examiner — David A Saunders
(74) Attorney, Agent, or Firm — McDonnell Boehnen Hulbert & Berghoff LLP

(57) ABSTRACT

The present invention provides a homogeneous assay for identifying an antibody producing cell producing an antibody which binds to a selected antigen comprising: a) providing a population of antibody producing cells; b) incubating said population of antibody producing cells with a selected antigen and a labeled anti-antibody antibody, wherein said anti-antibody antibody is capable of distinguishing cells producing an antibody which binds to the selected antigen from those cells which do not; and c) identifying an antibody producing cell capable of producing an antibody which binds to the selected antigen.

17 Claims, 5 Drawing Sheets

OTHER PUBLICATIONS

Van Mourik, P., et al., "Improved hybridoma technology: spleen cell separation and soluble growth factors," *Methods in Enzymology*, Langone, J.J., et al. (Eds.), *Academic Press Inc.*, N.Y., 1986, 121, 174-182.

Verma, R., et al., "Antibody engineering: comparison of bacterial, yeast, insect and mammalian expression systems," *J. of Immunol. Methods*, 1998, 216, 165-181.

Sung, W. B. et al., "Influence of fluorescent antibody probe specificity on flow cytometric analysis of antibody-producing cells", Journal of Immunological Methods, 1996, 189(1), 83-88.

Ward, E. S. et al., "Binding activities of a repertoire of single immunoglobulin variable domains secreted from *Escherichia coli*", Nature, 1989, vol. 341, 544-547.

\* cited by examiner (a)                                         (b)

(a)                          (b)

(a)                      (b)

(a)  (b)

ASSAY FOR IDENTIFYING ANTIBODY PRODUCING CELLS

The present invention relates generally to improved methods for producing antibodies and more specifically provides a homogeneous assay for obtaining antibodies.

The selected lymphocyte antibody method (SLAM) for generating monoclonal antibodies overcomes the limitations of both hybridoma technology and bacterially expressed antibody libraries by enabling high affinity antibodies generated during in vivo immune responses to be isolated from any species (Babcook et al., 1996, *Proc. Natl. Acad. Sci*, 93, 7843-7848). SLAM enables a single lymphocyte that is producing an antibody with a desired specificity or function to be identified within a large population of lymphoid cells and the genetic information that encodes the specificity of the antibody to be rescued from that lymphocyte. Antibody producing cells which produce antibodies which bind to selected antigens are detected using an adapted hemolytic plaque assay method (Jerne and Nordin, 1963, *Science*, 140, 405). In this assay erythrocytes are coated with the selected antigen and incubated with the population of antibody producing cells and a source of complement. Single antibody producing cells are identified by the formation of hemolytic plaques. Plaques of lysed erythrocytes are identified using an inverted microscope and the single antibody producing cell of interest at the centre of the plaque is removed using micromanipulation techniques and the antibody genes from the cell are cloned by reverse transcription PCR. Other methods for detecting single antibody-producing cells of a desired function have already been described in International Patent Specification, WO 92/02551.

In the hemolytic plaque assay described above the red blood cells are typically coated with antigen via a biotin/streptavidin coupling system that requires the antigen to be biotinylated. This method is therefore restricted to antigens that are available in a pure form and to those that can be biotinylated without affecting epitope presentation. This method clearly precludes the isolation of antibodies against a wide range of antigens. For example, many proteins are difficult to purify, particularly cell surface expressed proteins, such as type III proteins. Many proteins alter their conformation and presentation of desirable eptiopes upon biotinylation, for example proteins that contain lysine groups in their active site.

It may also be desirable to produce antibodies against unknown antigens, such as proteins expressed on the surface of cells, such as tumor cells. The direct use of tumor cells in the plaque assay instead of antigen coated erythrocytes is difficult to achieve given the requirement for cell lysis to occur in order for plaques contaning antibody producing cells to be identified. Cell lysis is dependent on cell type, antigen and antibody concentration. Red blood cells coated with the desired antigen will bind large amounts of available antibody and will lyse readily in the presence of complement. Other cell types such as tumor cells will not lyse so readily, especially when the availability of antigen on the surface may be very low and hence antibody binding will be low.

The current invention addresses these difficulties by providing improved methods for producing antibodies and more specifically by providing a homogeneous assay for obtaining antibodies. This improved assay has many advantages over the methods described above, allowing the identification of antibodies that bind to any antigen, including unknown antigens, cell surface antigens and antigens which cannot be biotinylated without altering the presentation of desirable epitopes. As a result, antibodies with binding specificities that were previously unidentifiable by conventional plaque assays can now be produced. In addition the assay is more facile than the hemolytic plaque assay and antibody producing cells can be identified more quickly.

We have demonstrated that it is possible to obtain antibody producing cells producing antibodies which bind to an antigen by incubating a population of antibody producing cells with an antigen source in the presence of labeled antibodies which bind to the antibodies produced by the antibody producing cells. Suprisingly, it is possible to distinguish those cells producing antibodies which bind to an antigen over those which do not without the need for wash steps to remove unbound label. Thus, according to the present invention, there is provided a homogeneous assay for identifying an antibody producing cell producing an antibody which binds to a selected antigen comprising:

a) providing a population of antibody producing cells;
b) incubating said population of antibody producing cells with a selected antigen and a labeled anti-antibody antibody, wherein said anti-antibody antibody is capable of distinguishing cells producing an antibody which binds to the selected antigen from those cells which do not; and
c) identifying an antibody producing cell producing an antibody which binds to the selected antigen.

The term 'antibody' as used herein includes any recombinant or naturally occurring immunoglobulin molecule such as a member of the IgG class e.g. IgG1 and also any antigen binding immunoglobulin fragment, such as Fv, Fab' and F(ab')$_2$ fragments, and any derivatives thereof, such as single chain Fv fragments.

The term 'antibody producing cell' as used herein means any cell capable of secreting an antibody, such as a B-lymphocyte, a plasma cell, a plasmablast, an activated B cell or a memory B cell. Antibody-producing cells for use in the invention may be obtained from an animal which has either been immunized with an antigen, or which has developed an immune response to an antigen as a result of disease. Other antibody producing cells for use in the present invention may include any transformed cell in particular, any mammalian cells which express immunoglobulin genes or parts thereof. In one example the populations of antibody producing cells for use in the present invention produce a range of antibodies with different binding specificities.

The assay of the present invention may also be used to identify high yielding antibody producing cells from a population of antibody producing cells which all produce the same antibody. The term 'high yielding' as used herein refers to antibody producing cells that produce antibodies of a known specificity but for which it would be desirable to identify those cells producing the antibody most efficiently. Identification of the high yielding cell will allow the cell to be isolated and clonally reproduced. In one example the high yielding antibody producing cell is a hybridoma cell. In another example the high yielding antibody producing cell is a transformed cell in particular, a mammalian cell which expresses immunoglobulin genes or parts thereof. Examples of such mammalian cells include but are not limited to NS0, CHO, COS and 293 cells.

The term 'antigen' as used herein refers to any known or unknown substance that can be recognised by an antibody, including proteins, glycoproteins and carbohydrates. Preferably these antigens include biologically active proteins, such as hormones, cytolines, and their cell surface receptors, bacterial or parasitic cell membranes or purified components thereof, and viral antigens. In one example the antigen is available in a pure form obtained either by direct purification from the native source or by recombinant expression and purification of said antigen. Preferably the purified antigen is coupled to erythrocytes or any other particle such as a bead for incorporation into the assay. In another example the antigen is one which is difficult to purify, such antigens include but are not limited to cell surface expressed proteins such as receptors, particularly type III proteins. In another example the presentation of desirable epitopes on the antigen is altered upon biotinylation, this includes but is not limited to proteins which contain lysines in their active site regions. In another example the antigen may be expressed on the surface of a cell, either naturally or recombinantly. Such cells may include but are not limited to mammalian cells, immunomodulatory cells, lymphocytes, monocytes, polymorphs, T cells, tumor cells, yeast cells, bacterial cell, infectious agents, parasites, plant cells, transfected cells such as NS0, CHO, COS, 293 cells. In one example the antigens expressed on the surface of said cells are antigens which are difficult to purify or antigens which lose desired epitopes upon biotinylation such as those antigens described above.

In another example the antigen is a cell or a population of cells for which it would be desirable to isolate antibodies to, such as mammalian cells, immunomodulatory cells, lymphocytes, monocytes, polymorphs, T cells, tumor cells, yeast cells, bacterial cell, infectious agents, parasites, and plant cells. In one embodiment the cell is a tumor cell.

The term 'homogeneous assay' as used herein refers to an assay whereby all components of the assay are combined together to identify antibody producing cells without the need to remove unbound labeled anti-antibody antibodies. The term 'labeled anti-antibody antibody' refers to labeled antibodies which bind to any region of the antibodies produced by the antibody producing cells, regardless of the binding specificity of those antibodies. Preferably said anti-antibody antibodies are from one species while the antibody producing cells are from another. Preferably these antibodies bind to the Fc portion of the antibody produced by the antibody producing cell.

The labeled anti-antibody antibodies are capable of distinguishing cells producing antibodies that bind to the selected antigen from those cells that do not. Appropriate labels are well known in the art and can include but are not limited to chemiluminescence, enzyme and fluorescent labels. Preferably the label is a fluorescent label. The fluorescent label conjugated to the anti-antibody antibodies can be any fluorescent label including but not limited to Aqua, Texas-Red, FITC, rhodamine, rhodamine derivative, fluorescein, fluorescein derivative, cascade blue, Cy5 and phycoerythrin. Preferably the fluorescent conjugate is FITC. Thus in one particular example of an assay according to the present invention, the antibody producing cells are from rabbits and the labeled anti-antibody antibodies are fluorescent labeled goat anti-rabbit anti-Fc antibodies.

In the assay of the present invention the antibody producing cells producing antibodies which bind to the selected antigen are distinguished from those that do not by detecting the increased concentration of labeled anti-antibody antibodies surrounding said cells. Preferably this is achieved by visualising the labeled anti-antibody antibodies and hence the antibody producing cell surrounded by said antibodies. In one example this is achieved using a microscope. Preferably the label is detected using an inverted microscope with a mercury vapour UV lamp and a filter set appropriate for the conjugate used. Preferably the filter set is a fluorescein filter set. Thus in one example, where the label is a fluorescent label the antibody producing cells producing antibodies which bind to the selected antigen are identified by a localised increase in fluorescence surrounding said cells. The present invention also provides a method of producing an antibody which binds to a selected antigen comprising:

a) providing a population of antibody producing cells;
b) incubating said population of antibody producing cells with a selected antigen and a labeled anti-antibody antibody, wherein said anti-antibody antibody is capable of distinguishing cells producing an antibody which binds to the selected antigen from those cells which do not;
c) identifying an antibody producing cell producing an antibody which binds to the selected antigen;
d) isolating the identified antibody producing cell; and optionally
e) synthesizing an antibody therefrom.

Where desired, steps (d) and (e) can be repeated more than once to isolate more than one antibody producing cell and to synthesize more than one antibody. The present invention therefore extends to at least one antibody producing cell identified by the above method and at least one antibody synthesized from said cell(s).

Antibody producing cells identified using the homogeneous assay described herein are isolated directly from the assay using micromanipulation techniques well known in the art.

Antibodies can be synthesized from the isolated antibody producing cell either directly or indirectly. Direct synthesis can be achieved by culturing the isolated antibody producing cell in an appropriate medium. Indirect synthesis can be achieved by isolating the genes encoding the antibodies or parts thereof and expressing them in a host cell using methods well known in the art. A vector containing the antibody gene(s) is transfected into a host cell and the host cell cultured in an appropriate medium such that the antibody or antibody fragment with the desired specificity is produced in the host cell.

DETAILED DESCRIPTION OF THE ASSAY

Antibody-producing cells for use in the present invention may be obtained from any appropriate source, including an animal which has either been immunized with a selected antigen, or which has developed an immune response to an antigen as a result of disease.

Animals may be immunized with a selected antigen using any of the techniques well known in the art suitable for generating an immune response (see Handbook of Experimental Immunology, D. M. Weir (ed.), Vol 4, Blackwell Scientific Publishers, Oxford, England, 1986). Many warm-blooded animals, such as humans, rabbits, mice, rats, sheep, cows or pigs may be immunized in order to obtain antibody-producing cells. However, mice, rabbits and rats are generally preferred.

High numbers of antibody producing cells can be found in the spleen and lymph node of the immunised animal and once an immune response has been generated and the animal has been sacrificed, the spleen and lymph nodes are removed. A single cell suspension of antibody producing cells is prepared using techniques well known in the art. Antibody producing cells can also be obtained from an animal that has generated the cells during the course of a disease. For instance, antibody producing cells from a human with a disease of unknown cause, such as cancer, may be obtained and used to assist in the identification of antibodies which have an effect on the disease process or which may lead to identification of an agent or body component that is involved in the cause of the disease. Similarly, antibody-producing cells may be obtained from subjects with disease of known cause such as malaria or AIDS. These antibody producing cells may be derived from the blood or lymph nodes, as well as from other diseased or normal tissues.

Antibody producing cells may also be obtained by culture techniques such as in vitro immunization. Examples of such methods are described by C. R. Reading in Methods in Enzymology 121:18-33 (J. J. Langone, H. H. van Vunakis (eds,), Academic Press Inc., N. Y.). Antibody producing cells may also be obtained from very early monoclonal or oligoclonal fusion cultures produced by conventional hybridoma technology. The population of antibody producing cells may be enriched for use in the assay by methods based upon the size or density of the antibody producing cells relative to other cells. An example of the use of Percoll to separate cells according to density is described by van Mourik and W. P. Zeizlmaker in Methods in Enzymology 121; 174-182 (J. J. Langone, H. H. van Vunakis (eds.), Academic Press Inc., N.Y.). Gradients of varying density of solutions of bovine serum albumin can also be used to separate cells according to density. (See N. Moav and T. N. Harris, J. Immunol. 105, 1512, 1970; see also Raid, D. J. in Selected Methods in Cellular Immunology, B. Misheli and S. Shiigi (eds.), W. H. Freeman and Co., San Francisco, 1987). Preferably separation is achieved by centrifugation with Ficoll-Hypaque (Pharmacia, Uppsula, Sweden). The fraction that is most enriched for desired antibody-producing cells can be determined in a preliminary procedure using ELISA based assays to select populations that may contain antibodies with the desired binding specificity. Alternatively or in addition, the fraction most enriched for the desired antibody can be determined by a functional assay.

In the assay the population of antibody producing cells suspected of producing antibodies with the desired binding specificity are suspended in an appropriate medium before incorporation into the assay. An appropriate medium for the assay will be one that provides at least the minimum requirements for short-term maintenance of cellular integrity and cellular structures, such as an isotonic buffer. Preferably this medium is immune cell medium comprising Roswell Park Memorial Institute medium (RPMI)+10% foetal bovine serum; 50 µM 2-β-mercaptoethanol; 2 mM glutamine; 20 mM Hepes; and 1× Penicillin and Streptomycin.

Under such conditions the antibody producing cells produce and secrete antibodies. Antibody producing cells are diluted within the medium to a density which allows selection of an individual or small number of antibody producing cells. If it is unclear which cell is responsible for the activity indicated by the assay, or in order to confirm the activity, the selected cell(s) may be retested for their ability to produce antibodies with the desired binding specificity.

The antigen for use in the assay may be, as described above, any substance to which an antibody can be produced including proteins, glycoproteins, carbohydrates and whole cells, such as tumor cells or transfected cells expressing the antigen on the surface. In one example the antigen is known and available in a pure form and is coated on the surface of erythrocytes or other particles such as beads for incorporation into the assay. A number of methods for coating particles with antigens are known to those skilled in the art. These include chromic chloride or water soluble carbodiimide. In one embodiment, a biotin/streptavidin coupling system is used to couple antigen to erythrocytes, the methods for which are described in detail in WO92/02551.

In another example the antigen is coupled to commercially available beads (for example as can be obtained from New England Biolabs). Antigen can be conjugated to beads using a number of different methods, preferably via direct conjugation to activated beads or via biotin to streptavidin-coupled beads. Preferably these beads are magnetic for ease of handling.

In another example, particularly when the antigen loses desirable epitopes upon biotinylation, the antigen is coupled to the surface of a particle via a polyclonal antibody that binds the antigen. To prepare the antigen-polyclonal antibody-particle conjugate, the polyclonal antibody is first conjugated to the surface of a particle, such as a bead using any suitable method, such as via biotin to streptavidin-coupled beads. The polyclonal antibody-particle conjugate is then incubated with an excess of antigen to allow binding of the polyclonal antibody to the antigen. The antigen-polyclonal antibody-particle conjugate is then separated from unbound antigen, for example by centrifugation, and incorporated into the assay. The polyclonal antibody for use in the conjugate may be produced using any suitable method known in the art, using the desired antigen as immunogen, in any suitable species. The polyclonal antibody may be a whole IgG or a fragment thereof such as a Fab', F(ab')$_2$ or Fab fragment. Fragments may be produced using any method known in the art, for example by pepsin or papain digestion. It is important that the polyclonal antibody used in the conjugate is not recognized by the labeled anti-antibody antibody used in the assay to detect the antibodies produced by the antibody producing cells. For example where the antibody producing cells are from rabbit, the labeled anti-antibody antibody may be an anti-rabbit anti-Fc antibody and the polyclonal antibody used in the conjugate should be an antibody from a species other than rabbit, for example goat, or if the antibody is from rabbit it should be a fragment lacking the Fc region, for example a Fab', F(ab')$_2$ or Fab fragment.

In another example, particularly when the antigen is difficult to purify or loses desired epitopes upon biotinylation the antigen is expressed on the surface of a cell. Such cells may be those that naturally express the antigen on their surface or a transfected cell expressing the antigen on its surface. Such cells may include but are not limited to mammalian cells, immunomodulatory cells, lymphocytes, monocytes, polymorphs, T cells, tumor cells, yeast cells, bacterial cell, infectious agents, parasites, plant cells, transfected cells such as NS0, CHO, COS, 293 cells. Transfection of cells such as NS0, CHO, COS and 293 cells can be achieved by any method known in the art including, electroporation and nucleofection.

In a further example the antigen source is any cell that it would be desirable to isolate antibodies to. Such cells may include but are not limited to mammalian cells, immunomodulatory cells, lymphocytes, monocytes, polymorphs, T cells, tumor cells, yeast cells, bacterial cell, infectious agents, parasites and plant cells.

The antibody producing cells and the antigen are incorporated into the assay at an appropriate concentration which can be determined empirically for example as described in the examples hereinafter. The antibody producing cells are at sufficiently low density that they are well separated allowing identification and isolation of the antibody producing cell producing antibodies of the desired specificity. The antigen will be present in excess and preferably the antigen is in a 10-1,000 fold excess over the antibody producing cells.

In order to identify antibodies that bind to the selected antigen, labeled anti-antibody antibodies are incorporated into the assay. Said antibodies will bind to all antibodies produced by the antibody producing cells, regardless of their binding specificity. Such antibodies are easily produced by one skilled in the art or are readily available commercially. Preferably the anti-antibody antibodies are anti-Fc antibodies. In one embodiment of the present invention the antibody producing cells are from rabbits and the labeled anti-Fc antibodies are goat anti-rabbit anti-Fc antibodies.

The label conjugated to the anti-antibody antibodies is any label that can be detected in the assay by any suitable method known in the art. Many different conjugates are available for labeling the antibodies for example, chemiluminescent, enzyme and fluorescent labels. Such antibodies are easily produced by one skilled in the art or are readily available commercially. Preferably the label is one that can be detected by microscopy. In general in the various aspects of the invention described herein the label used is preferably a fluorescent label. Particular fluorescent labels are those which can be visualised by microscopy and can include but are not limited to Aqua, Texas-Red, FITC, rhodamine, rhodamine derivatives, fluorescein, fluorescein derivatives, cascade blue, Cy5 and phycoerythrin. Preferably said label is the fluorescent conjugate, fluorescein isothiocyanate (FITC). The labeled anti-antibody antibody is used in the assay at a concentration at which it is possible to distinguish cells producing antibodies that bind to the selected antigen from those cells that do not. The optimal concentration can be determined empirically by one skilled in the art by varying the concentration of labeled anti-antibody antibody. In one example the labeled antibody is a fluorescent labeled antibody and is used at a concentration that is not so low that no fluorescence can be detected and not so high that there is high background fluorescence. Preferably the fluorescent labeled anti-antibody antibody is in excess such that it binds all antibodies produced by the antibody producing cell without causing excessive background fluorescence.

To identify antibody producing cells producing antibodies which bind to the selected antigen the assay mixture comprising a population of antibody producing cells, the antigen and labeled anti-antibody antibody is incubated in the medium described above to allow binding to take place. Optimal incubation times and temperatures can be determined empirically by one skilled in the art. Incubation will take place in any suitable container such as a microscope slide at any suitable temperature for example between 4° C. or about and 37° C. or about, for any suitable length of time for example between 5 minutes or about and 5 hours or about. Preferably the incubation of the assay mixture takes place on a microscope slide at 37° C. for up to 1 hour.

The labeled anti-antibody antibody is detected using any appropriate method known in the art. Preferably the labeled anti-antibody antibody is detected using a microscope. More preferably the anti-antibody antibody is conjugated to a fluorescent label and the fluorescence is visualised using an inverted microscope equipped with a mercury vapour UV lamp with an appropriate filter set. Preferably the filter set is a fluorescein filter set.

Antibody producing cells which produce an antibody which binds to the selected antigen are identified by the increased concentration of labeled anti-antibody antibodies surrounding the cell. Those antibody producing cells producing antibodies which do not bind to the antigen will not be surrounded by an increased concentration of labeled anti-antibody antibodies. High yielding antibody producing cells are identified as those where the localised increase in anti-antibody antibody concentration appears most quickly.

The antibody producing cell may then be isolated directly from the assay using standard micromanipulation techniques such as a fine glass pipette and a micromanipulator. Antibodies can be synthesized directly or indirectly from the isolated antibody producing cell. Direct synthesis can be achieved by culturing the isolated antibody producing cell in an appropriate medium. If the assay is used to identify a high yielding antibody producing cell the cell will be cultured under appropriate conditions to clonally reproduce this high yielding cell.

Indirect synthesis can be achieved by isolating the genes encoding the antibodies or parts thereof and expressing them in a host cell. The entire genes may be cloned or the variable regions or portions thereof which confer the desired specificity of the antibody may be cloned and used to produce recombinant antibodies. Recombinant antibodies can take several different forms and include intact immunoglobulins, chimeric antibodies, humanised antibodies and antigen binding fragments such as Fv, Fab, Fab' and F(ab')$_2$ fragments, and any derivatives thereof, such as single chain Fv fragments. The methods for creating these antibody molecules are well known in the art (see for example, Boss, U.S. Pat. No. 4,816, 397; Shrader, WO 92/02551; Ward et al., 1989, *Nature*, 341, 544; Orlandi et al., 1989, *Proc. Natl. Acad. Sci. USA*, 86, 3833; Morrison et al., 1984, *Proc. Natl. Acad. Sci. USA*, 81, 6851; Riechmann et al., 1988, *Nature*, 322, 323; Bird et al, 1988, *Science*, 242, 423). The types of expression systems available to produce these antibody molecules include bacterial, yeast, insect and mammalian expression systems, the methods for which are well known in the art (Verma et al., 1998, *Journal of Immunological Methods*, 216, 165-181).

Antibodies obtained according to the invention may be used without further modification, or if desired following modification including conjugation to one or more reporter or effector molecules, for any suitable diagnostic or therapeutic purpose.

ICM—immune cell medium (RPMI+10% foetal bovine serum; 50 µM 2-β-mercaptoethanol; 2 mM glutamine; 20 mM hepes; and 1× penicillin and streptomycin)
RPMI—Roswell Park Memorial Institute medium
PBS—Phosphate buffered saline

EXAMPLE 1

Identification of Specific Antibody Producing B-cells Using Antigen Coated Sheep Red Blood Cells (SRBC)
Antigen Coating of SRBC The coating of the SRBC (obtained from TCS Biosciences) was carried out by streptavidin linking the biotinylated antigen to the surface of biotin coated SRBC. The antigen coated SRBC were prepared on the day of use and stored 5% (v/v) in immune cell medium.

Identification of Antigen Specific Antibody Secreting B-Cells

The assay mix was set up in ICM and contained 10 µl of rabbit B cells containing 10-1,000 B cells from an ELISA positive population, 10 µl antigen coated SRBC (5% v/v) and 20 µl of Goat anti-Rabbit IgG Fc specific FITC conjugate (Jackson ImmunoResearch) at variable concentrations for each experiment (1:100, 1:200, 1:400 and 1:800). The experiments were set up to determine the optimal concentration of Goat anti-Rabbit IgG Fc specific FITC conjugate required for the identification of antibody producing cells without excessive background fluorescence.

Figure 1:
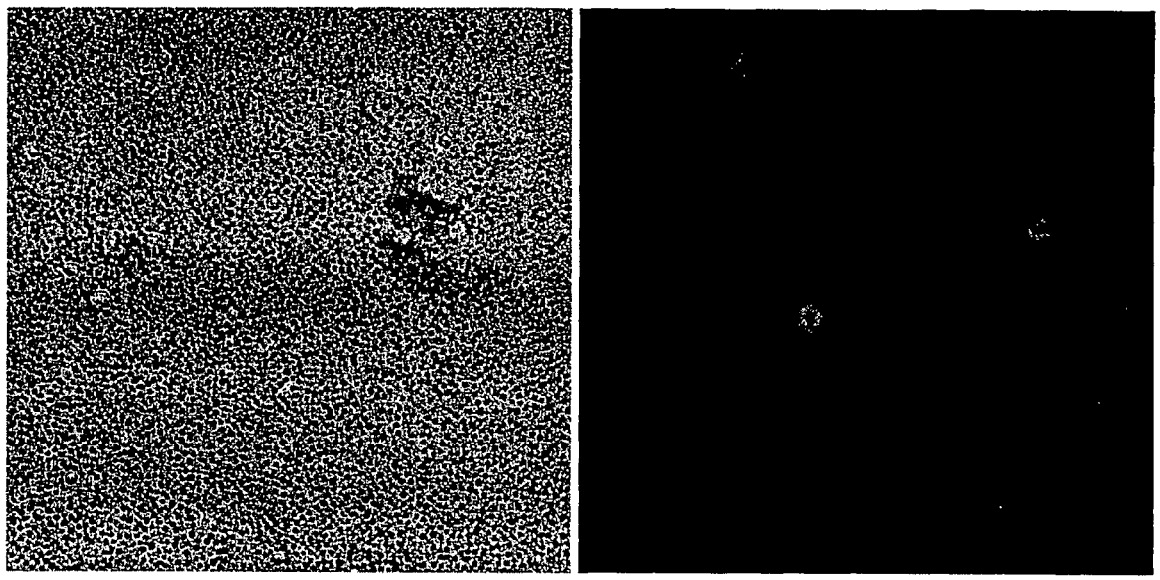
FIG. 1 A homogeneous fluorescence assay comprising rabbit B cells, sheep red blood cells coated with antigen and Goat anti-Rabbit IgG Fc specific FITC conjugate. Assay visualised using an inverted microscope equipped with a mercury vapour UV lamp and fluorescein filter set. Magnification ×8.
(a) Phase image of assay.
(b) Fluorescence image of assay. Fluorescence localised around B cells secreting antigen specific antibodies FIG. 2 A homogeneous fluorescence assay comprising rabbit B cells, magnetic beads coated with antigen and Goat anti-Rabbit IgG Fc specific FITC conjugate. Assay visualised using an inverted microscope equipped with a mercury vapour UV lamp and fluorescein filter set. Magnification ×20.
(a) Phase image of assay.
(b) Fluorescence image of assay. Fluorescence localised around B cells secreting antigen specific antibodies FIG. 3 ELISA detection of specific antigen binding of antibodies produced in CHO cells.

This assay mix was then spotted (2-3 µl per spot), onto Sigmacote® treated 'chamber' slides and flooded with light paraffin oil. Slides were incubated for 20-30 mins at 37° C. and examined using an inverted microscope equipped with a mercury vapour UV lamp and a fluorescein filter set. B cells, (plasma cells), secreting antigen specific IgG antibody were identified by a focal increase in fluorescence surrounding said cells. See FIG. 1. Using this method the optimal concentration for Goat anti-Rabbit IgG Fc specific FITC conjugate was found to be 1:400. Other B cells in the mixture, which did not secrete antigen specific antibodies, did not show surrounding fluorescence. In SRBC controls where no antigen was present on the surface, no B-cell localised fluorescence was observed. The B cells present within the fluorescent foci were then harvested into Eppendorf tubes using standard micro-manipulation apparatus, (Eppendorf Transferman and CeilTram Vario) and the heavy and light chain variable regions of the antibody subsequently isolated by PCR.

EXAMPLE 2

Identification of Specific Antibody Producing B Cells Using Antigen Coated Beads
1 µM magnetic streptavidin coated beads, (New England Biolabs), were used in all experiments.
Determination of Optimal Density for Bead Monolayer.

An aliquot of the bead stock was washed 3× in PBS to remove preservative, using a magnet, and resuspended in the same volume of immune cell medium, (ICM), (RPMI+10% foetal bovine serum; 50 µM 2-β-mercaptoethanol; 2 mM glutamine; 20 mM Hepes; and 1× Penicillin and Streptomycin).

Serial 2-fold dilutions of beads were prepared in ICM and used to determine a dilution with a bead density that produced an even monolayer when the beads were spotted (2-3 ul per spot) onto Sigmacote treated slides and overlaid with light paraffin oil. A final dilution of washed beads of ⅛ was determined to be optimal.

Antigen Loading onto Beads and Identification of Antigen Specific B Cells.

50 µl aliquots of streptavidin coated beads were washed and resuspended in 50 µl PBS. Each aliquot was incubated with different amounts of stock biotinylated antigen (1 mg/ml) ranging from 0.1 µg up to 25 µg. These were incubated for 1 h at room temperature with occasional manual shaking. The beads were then washed in PBS using a magnet and resuspended in 50 µl of ICM.

20 µl of the antigen loaded beads were then mixed with 40 µl of ELISA positive B cells; 60 µl of ICM; and 40 µl of a ¹⁄₄₀₀ dilution of a Goat anti-Rabbit IgG Fc specific FITC conjugate (Jackson ImmunoResearch).

This mixture was then spotted, (2-3 µl per spot), onto Sigmacote treated 'chamber' slides and flooded with light paraffin oil. Slides were incubated for 20-30 mins at 37° C. and examined using an inverted microscope equipped with a mercury vapour UV lamp and a fluorescein filter set.

Figure 2:
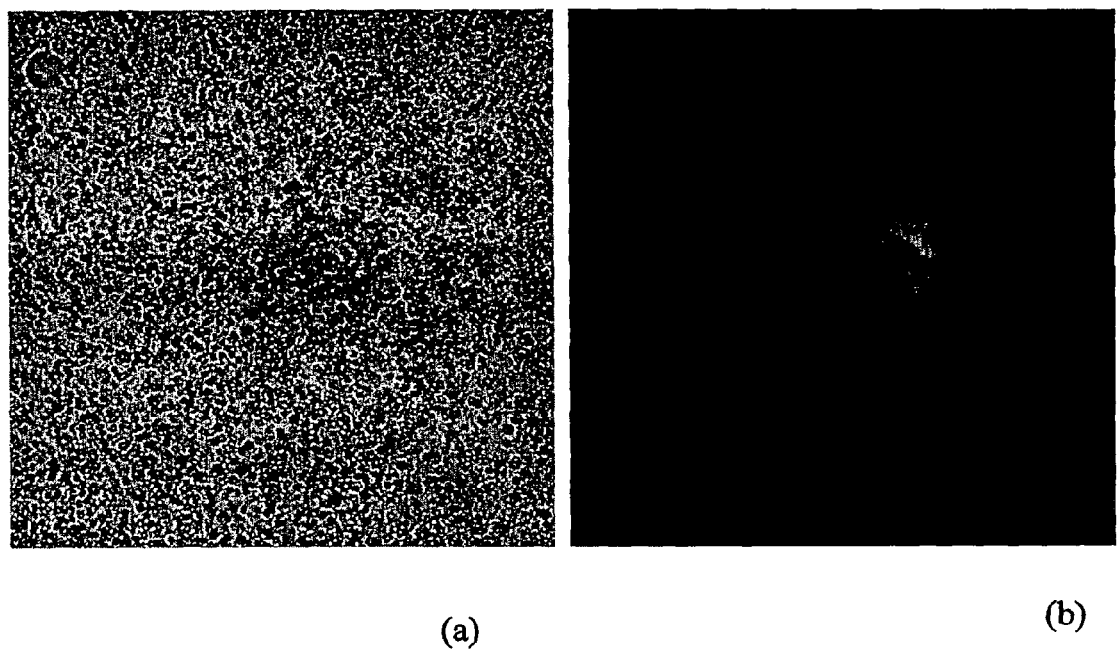

B cells, (plasma cells), secreting antigen specific IgG antibody were identified by a focal increase in fluorescence around the B cell. See FIG. 2. Using this method 1 µg of biotinylated antigen per 50 µl of bead stock was determined as optimal for signal generation for this particular antigen. Other B cells in the mixture, which did not secrete antigen specific antibodies, did not show surrounding fluorescence. In controls, no B-cell localised fluorescence was observed when the beads were coated with another irrelevant antigen.

Figure 3:
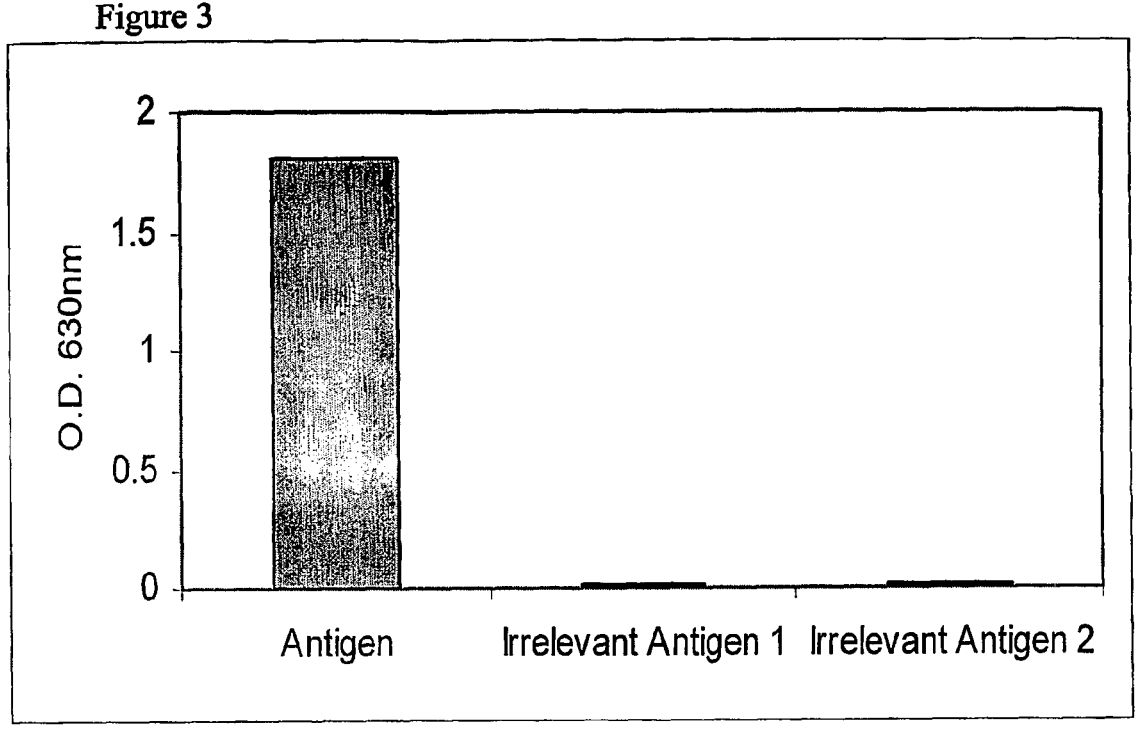

The B cells present within the fluorescent foci were then harvested into Eppendorf tubes using standard micro-manipulation apparatus, (Eppendorf Transferman and CellTram Vario) and the heavy and light chain variable regions of the antibody from one of the cells subsequently isolated by PCR. A recombinant chimeric IgG (human constant regions) was produced by transient expression in CHO cells. Transfections of CHO cells were performed using the lipofectamine procedure according to manufacturer's instructions (InVitrogen, catalogue no. 18324). Specific binding of th IgG to antigen was confirmed by ELISA (FIG. 3).

EXAMPLE 3

Identification of Specific Antibody Producing B-Cells Using Surface Expression of Antigen on COS-1 Cells
Transient Expression of Antigen on COS-1 Cells COS-1 cells transiently expressing the selected antigen were suspended in Immune cell media. Cell density was altered to $2 \times 10^7$ cells per ml.

Identification of Antigen Specific Antibody Secreting B-Cells

The assay mix was set up in ICM and contained 40 µl ELISA positive B cells, 40 µl of Goat anti-Rabbit IgG Fc specific FITC conjugate (Jackson hnmunoResearch) at 1:400 dilution and 40 µl of COS-1 cell suspension.

This assay mix was then spotted (2-3 ul per spot), onto Sigmacote treated 'chamber' slides and flooded with light paraffin oil. Slides were incubated for 40 mins at 37° C. and examined using an inverted microscope equipped with a mercury vapour UV lamp and a fluorescein filter set.

Figure 4:
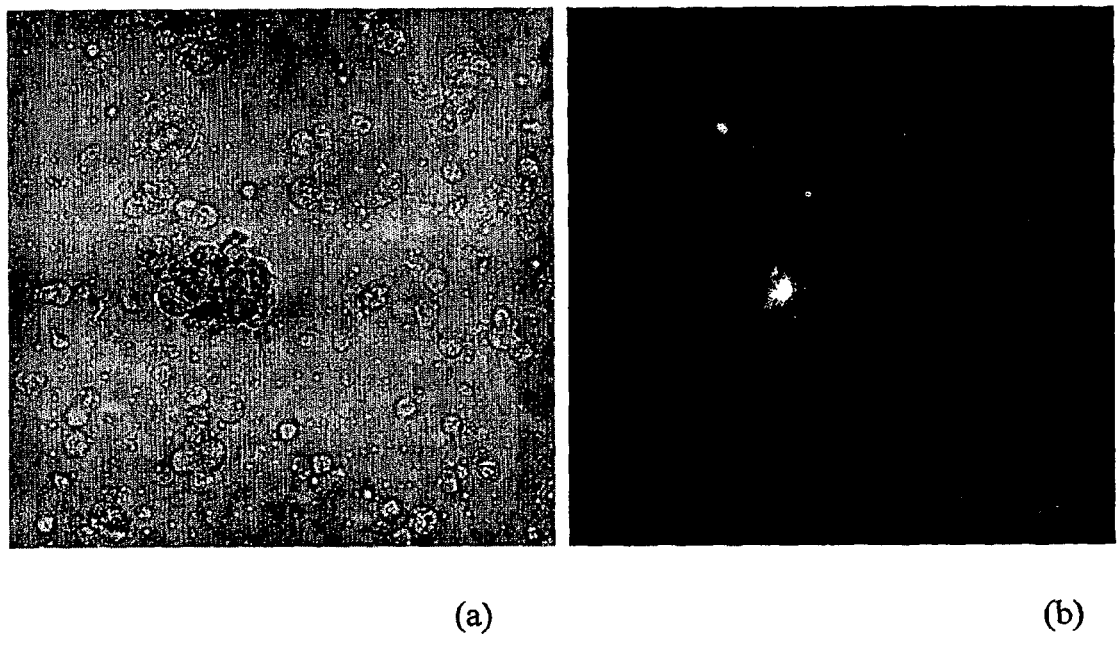
FIG. 4 A homogeneous fluorescence assay comprising rabbit B cells, transfected COS-1 cells expressing antigen on their surface and Goat anti-Rabbit IgG Fc specific FITC conjugate. Assay visualised using an inverted microscope equipped with a mercury vapour UV lamp and fluorescein filter set. Magnification ×8
(a) Phase image of assay.
(b) Fluorescence image of assay. Fluorescence localised around B cells secreting antigen specific antibodies.

B cells, (plasma cells), secreting antigen specific IgG antibody were identified by a focal increase in fluorescence surrounding the B cells. See FIG. 4. Other B cells in the mixture, which did not secrete antigen specific antibodies, did not show surrounding fluorescence. In COS-1 cell controls where no antigen was present on the surface, no B-cell localised fluorescence was observed.

The B cells present within the fluorescent foci were then harvested into Eppendorf tubes using standard micro-manipulation apparatus, (Eppendorf Transferman and CellTram Vario) and the heavy and light chain variable regions of the antibody subsequently isolated by PCR.

EXAMPLE 4

Identification of Specific Antibody Producing B-Cells Using Surface Expression of Antigen on Chinese Hamster Ovary (CHO) Cells
Transient Expression of Antigen on CHO Cells
CHO cells transiently expressing the selected antigen were suspended in Immune cell media. Cell density was altered to $2\times10^7$ cells per ml.
Identification of Antigen Specific Antibody Secreting B-Cells The assay mix was set up in ICM and contained 40 µl ELISA positive B cells, 40 µl of Goat anti-Rabbit IgG Fc specific FITC conjugate (Jackson ImmunoResearch) at 1:400 dilution and 40 µl of CHO cell suspension.

This assay mix was then spotted (2-3 µl per spot), onto Sigmacote treated 'chamber' slides and flooded with light paraffin oil. Slides were incubated for 40 mins at 37° C. and examined using an inverted microscope equipped with a mercury vapour UV lamp and a fluorescein filter set.

Figure 5:
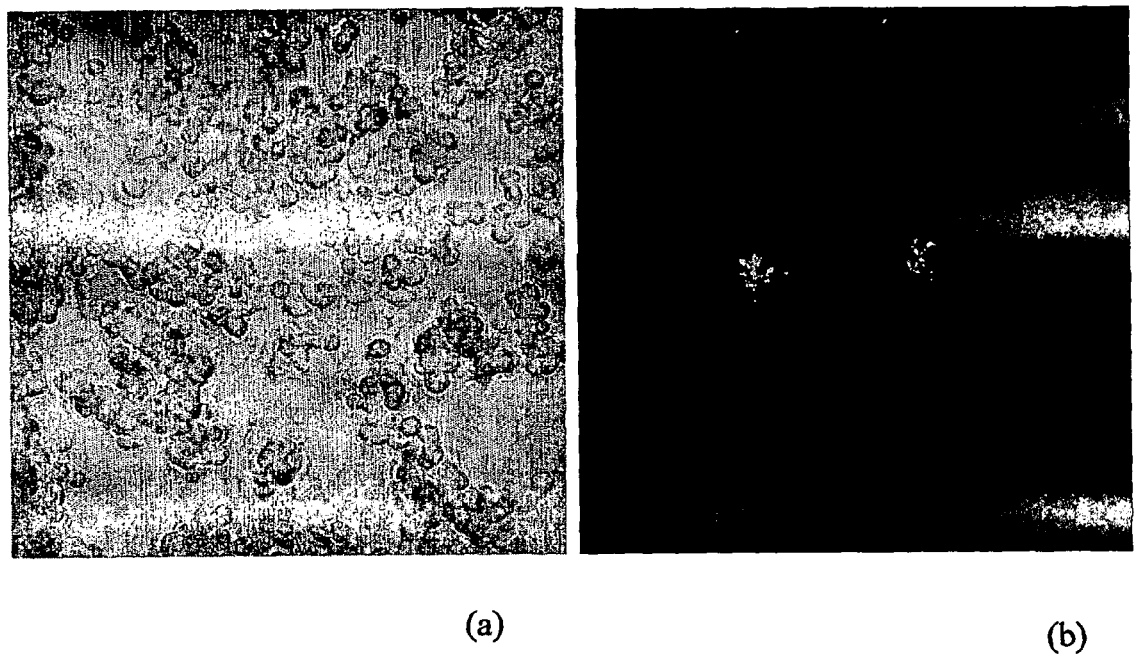
FIG. 5 A homogeneous fluorescence assay comprising rabbit B cells, transfected CHO cells expressing antigen on their surface and Goat anti-Rabbit IgG Fc specific FITC conjugate. Assay visualised using an inverted microscope equipped with a mercury vapour UV lamp and fluorescein filter set. Magnification ×8.
(a) Phase image of assay.
(b) Fluorescence image of assay. Fluorescence localised around B cells secreting antigen specific antibodies The following examples are offered by way of illustration, and not by way of limitation. The following abbreviations are used in the examples.

B cells, (plasma cells), secreting antigen specific IgG antibody were identified by a focal increase in fluorescence surrounding the B cells. See FIG. 5. Other B cells in the mixture, which did not secrete antigen specific antibodies, did not show surrounding fluorescence. In CHO cell controls where no antigen was present on the surface, no B-cell localised fluorescence was observed.

The B cells present within the fluorescent foci were then harvested into Eppendorf tubes using standard micro-manipulation apparatus, (Eppendorf Transferman and CellTram Vario) and the heavy and light chain variable regions of the antibody subsequently isolated by PCR.

The invention claimed is:

1. A homogeneous assay for identifying an antibody producing cell that produces an antibody that binds to a selected antigen comprising:
   providing a population of antibody producing cells;
   incubating on a microscope slide the population of antibody producing cells with an antigen, said antigen being coupled to an erythrocyte or a particle, or said antigen being expressed on the surface of a cell, and a labeled anti-antibody antibody wherein the anti-antibody antibody distinguishes antibody producing cells that produce an antibody that binds to the selected antigen from antibody producing cells that do not and wherein the anti-antibody antibody binds to all antibodies produced by the antibody producing cells, regardless of their binding specificity; and
   without performing any wash steps, identifying an antibody producing cell that produces an antibody that binds to the selected antigen by detecting the increased concentration of labeled anti-antibody antibodies surrounding said antibody producing cell.

2. The assay of claim 1 where the antigen is coupled to an erythrocyte.

3. The assay of claim 1 where the antigen is coupled to a particle.

4. The assay of claim 3 where the antigen is coupled to a particle via a polyclonal antibody.

5. The assay of claim 4 where the polyclonal antibody is an antibody fragment.

6. The assay of claim 5 where the polyclonal antibody is an antibody Fab, Fab' or F(ab')$_2$ fragment.

7. The assay of claim 1 where the antigen is expressed on the surface of a cell.

8. The assay of claim 7 where the cell is a transfected cell.

9. The assay of claim 7 where the cell is a tumor cell.

10. The assay of claim 1 where the antigen is an infectious agent.

11. The assay of claim 1 where the labeled anti-antibody antibody is labeled is an anti-Fc antibody.

12. The assay of claim 1 where the labeled anti-antibody antibody is labeled with a fluorescent label.

13. The assay of claim 12 where the fluorescently-labeled anti-antibody antibody is labeled with FITC.

14. The assay of claim 13 where the FITC labeled anti-antibody antibody is an anti-Fc antibody.

15. The assay of claim 1 where the antibody producing cells are B cells, plasma cells, plasmablasts, activated B cells or memory B cells.

16. The assay of claim 1 where the antibody producing cell that produces an antibody is a hybridoma cell or a mammalian cell engineered to express antibodies.

17. A method for synthesizing an antibody that binds to a selected antigen comprising:
   providing a population of antibody producing cells;
   incubating on a microscope slide the population of antibody producing cells with an antigen, said antigen being coupled to an erythrocyte or a particle, or said antigen being expressed on the surface of a cell, and a labeled anti-antibody antibody, wherein the anti-antibody antibody distinguishes antibody producing cells that produce an antibody that binds to the selected antigen from antibody producing cells that do not and wherein the anti-antibody antibody binds to all antibodies produced by the antibody producing cells, regardless of their binding specificity;
   without performing any wash steps, identifying an antibody producing cell that produces an antibody that binds to the selected antigen by detecting the increased concentration of labeled anti-antibody antibodies surrounding said antibody producing cell;
   isolating the identified antibody producing cell that produces said antibody that binds to the selected antigen; and
   directly or indirectly synthesizing said antibody that binds to the selected antigen from the isolated antibody producing cell that produces said antibody.

* * * * *